United States Patent
Siemionow (10) Patent No.: US 12,391,927 B2
(45) Date of Patent: Aug. 19, 2025

(54) MULTI-CHIMERIC CELL AND THERAPY FOR TRANSPLANTATION AND TREATMENT OF IMMUNE DEFICIENCIES AND GENETIC DISORDERS

(71) Applicant: THE BOARD OF TRUSTEES OF THE UNIVERSITY OF ILLINOIS, Urbana, IL (US)

(72) Inventor: Maria Siemionow, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1026 days.

(21) Appl. No.: 16/761,561

(22) PCT Filed: Nov. 28, 2018

(86) PCT No.: PCT/US2018/062736
§ 371 (c)(1),
(2) Date: May 5, 2020

(87) PCT Pub. No.: WO2019/108584
PCT Pub. Date: Jun. 6, 2019

(65) Prior Publication Data
US 2020/0263141 A1    Aug. 20, 2020

Related U.S. Application Data

(60) Provisional application No. 62/591,397, filed on Nov. 28, 2017.

(51) Int. Cl.
| | |
|---|---|
| *C12N 5/16* | (2006.01) |
| *A61K 35/12* | (2015.01) |
| *A61K 35/28* | (2015.01) |
| *A61K 35/34* | (2015.01) |
| *A61K 40/10* | (2025.01) |
| *A61K 40/22* | (2025.01) |
| *A61K 40/41* | (2025.01) |
| *C12N 5/073* | (2010.01) |
| *C12N 5/078* | (2010.01) |

(52) U.S. Cl.
CPC .......... *C12N 5/16* (2013.01); *A61K 35/28* (2013.01); *A61K 35/34* (2013.01); *A61K 40/10* (2025.01); *A61K 40/22* (2025.01); *A61K 40/416* (2025.01); *A61K 40/418* (2025.01); *C12N 5/0605* (2013.01); *C12N 5/0634* (2013.01); *A61K 2035/122* (2013.01); *A61K 2035/124* (2013.01); *A61K 2239/31* (2023.05)

(58) Field of Classification Search
None
See application file for complete search history.

(56) References Cited

U.S. PATENT DOCUMENTS

| | | | | |
|---|---|---|---|---|
| 2003/0228289 | A1 * | 12/2003 | Siemionow | A61K 45/06 424/93.7 |
| 2016/0346330 | A1 | 12/2016 | Sussman | |

FOREIGN PATENT DOCUMENTS

| | | | | |
|---|---|---|---|---|
| WO | WO-03102126 A1 * | 12/2003 | ......... A61K 2300/00 |
| WO | WO-2011140654 A1 * | 11/2011 | ............ A61K 35/51 |
| WO | 2016201182 A1 | 12/2016 | |

OTHER PUBLICATIONS

Gorbe et al. Myoblast proliferation and syncytial fusion both depend on connexin43 function in transfected skeletal muscle primary cultures. Experimental Cell Research 313 (2007) 1135-1148 (Year: 2007).*

Cwykiel et al. Cellular Therapy Models: Ex Vivo Chimera Model by Cell Fusion. M.Z. Siemionow (ed.), Plastic and Reconstructive Surgery: Experimental Models and Research Designs. p. 593-603 (Year: 2015).*

Craig et al. Expression of Thy-1 on Human Hematopoietic Progenitor Cells. J. Exp. Med. vol. 177 May 1993 1331-1342 (Year: 1993).*

Tfaily et al. "In vitro and in vivo characterization of human hematopoietic chimeric cells—a novel strategy to induce tolerance in transplantation" (2016), Vascularized Composite Allotransplantation, vol. 3, 1-2: 29 (Year: 2016).*

Office communication dated May 27, 2022 in EP 18830033.9.

Cwykiel J. et al. "Characterization of Human Multi-Chimeric Cells a New Tolerance Inducing Cellular Therapy in Transplantation: A Preliminary Study" Abstracts of the 18th Congress of the European Society for Organ Transplantation Sep. 24-27, 2017 Barcelona, Spain Sep. 24, 2017 vol. 30 (suppl. 2)165-346 BOS476 p. 302.

Cwykiel, J. & M.Z. Siemionow (2015) "Cellular therapy models: ex vivo chimera model by cell fusion," Plastic and Reconstructive Surgery: Experimental Models and Research Designs, Siemionow (Ed.), Springer-Verlag London, Ltd. p. 593-603.

International Preliminary Report on Patentability in PCT/US2018/062736 dated Jun. 11, 2020.

International Search Report and Written Opinion in PCT/US2018/062736 dated Mar. 1, 2019.

(Continued)

*Primary Examiner* — Teresa E Knight (74) *Attorney, Agent, or Firm* — Licata & Tyrrell P.C.; Jane Massey Licata (57) ABSTRACT

A multi-chimeric cell created by ex vivo fusion of three or more hematopoietic stem cells, mesenchymal stem cells, myoblasts, pericytes, or satellite cells, or a combination thereof, from three or more different donors is provided, as is the use of these cells in transplant therapy and treatment of immune deficiency and genetic disorders.

6 Claims, 1 Drawing Sheet

(56) References Cited

OTHER PUBLICATIONS

Siemionow, M., J. Cwykiel & M. Madajka (2015) "Bone marrow-derived ex vivo created hematopoietic chimeric cells to support engraftment and maintain long-term graft survival in reconstructive transplantation," The Science of Reconstructive Transplantation, Springer Science Business Media, New York, p. 227-254.

Siemionow, M., M. Madajka & J.Cwykiel (2012) "Application of cell-based therapies in facial transplantation," Annals of Plastic Surgery 69(5):575-579.

* cited by examiner

MULTI-CHIMERIC CELL AND THERAPY FOR TRANSPLANTATION AND TREATMENT OF IMMUNE DEFICIENCIES AND GENETIC DISORDERS This application is a U.S. National Stage Application of PCT/US2018/062736 filed Nov. 28, 2018 and claims benefit of priority to U.S. Provisional Patent Application Ser. No. 62/591,397, filed Nov. 28, 2017, the contents of each of which are incorporated herein by reference in their entirety.

This invention was made with government support under grant no. W81XWH-13-2-0053 awarded by the Department of Defense. The government has certain rights in this invention.

INTRODUCTION

Background

Stem cell transplantation is a promising new strategy for the treatment of many human disorders. Hematopoietic stem cell (HSC) transplant is a most instructive example for the curative potential of stem cell-based therapies. While the autologous HSC may not be a treatment option for many hematological diseases, the availability of the allogeneic stem cell grafts is limited due to the lack of matched related donors. In addition, matched unrelated HSC transplants are hampered by often prohibitive mortality and morbidity due to the toxic effects of the conditioning regimens and graft-versus-host-disease (GvHD). Improvement of the engraftment rates or efficacy and ability to perform transplantation across the histocompatibility barrier without the risk of GvHD would greatly increase application of HSC transplantation as a new treatment modality of choice for many, often incurable diseases.

Chimeric cells have been developed by various ex vivo fusion methods (Siemionow, et al. (2012) *Ann. Plast. Surg.* 69(5):575-9; Cwykiel & Siemionow (2015) Plastic and Reconstructive Surgery: Experimental Models and Research Design, Siemionow (Ed.), Springer-Verlag London, Ltd., Chapters 71-72). Chimeric cell therapies applied in different experimental models, including the vascularized composite allotransplantation (VCA), irradiation and muscular dystrophy animal models have been described (Arslan, et al. (2007) *Microsurgery* 27:190-9; Kulahci, et al. (2010) *Transplantation* 90(8):843-52; Hivelin, et al. (2016) *Arch. Immunol. Ther. Exp.* (Warsz). 64(4):299-310; Siemionow, et al. (2016) *Microsurgery* 36(8):676-683).

SUMMARY OF THE INVENTION

This invention is a multi-chimeric cell composed of a fusion of three or more hematopoietic stem cells, mesenchymal stem cells, myoblasts, pericytes, satellite cells, or a combination thereof, from three or more different donors. In certain embodiments, the hematopoietic stem cells are isolated from bone marrow, umbilical cord blood, peripheral blood, or a combination thereof. In other embodiments, the donors are related, unrelated, or a combination thereof. In some embodiments, the fusion is a combination of a hematopoietic stem cell and two or more cells independently selected from hematopoietic stem cells and mesenchymal stem cells. In other embodiments, the fusion is a combination of a hematopoietic stem cell and two or more cells independently selected from hematopoietic stem cells, mesenchymal stem cells, and pericytes. In other embodiments, the fusion is a combination of a myoblast and two cells independently selected from mesenchymal stem cells, myoblasts, and satellite cells. In particular embodiments, the fusion is a combination of a hematopoietic stem cell, a mesenchymal stem cell and a pericyte; three hematopoietic stem cells; a myoblast, a mesenchymal stem, and a satellite cell; or three myoblast cells. A kit is also provided, which includes a fusogenic agent, and three or more donor cells selected from the group of hematopoietic stem cells, mesenchymal stem cells, myoblasts, pericytes, satellite cells, from three or more different donors.

The invention also provides a method of treating an immune deficiency or genetic disorder by administering to a subject in a subject in need of treatment an effective amount of the multi-chimeric cell of the invention. In some embodiments, the multi-chimeric cell is administered by intraosseous, intravenous, or intramuscular injection. In other embodiments, the immune deficiency or genetic disorder is selected from bone marrow failure, Adenosine Deaminase (ADA) deficiency, Severe Combined Immunodeficiency (SCID), DiGeorge Syndrome, Ataxia Telangectasia, muscular dystrophy, type I diabetes, Gaucher disease, leukemia, aplastic anemia, sickle cell anemia, lymphoma and multiple myeloma. In embodiments directed to the treatment of muscular dystrophy, is preferable that the multi-chimeric cell is composed of a fusion of a myoblast and two or more cells independently selected from mesenchymal stem cells, myoblasts, and satellite cells. In embodiments directed to the treatment of sickle cell anemia, it is preferable that the multi-chimeric cell is a fusion of a hematopoietic stem cell and two or more cells independently selected from hematopoietic stem cells and mesenchymal stem cells.

This invention further provides a method of preventing the development of GvHD or reducing the severity of GvHD in a subject receiving an allogeneic hematopoietic stem cell transplant or organ transplant by administering to the subject an effective amount of the multi-chimeric cell of the invention. In accordance with this aspect of the invention, it is preferable that the multi-chimeric cell is a fusion of a hematopoietic stem cell and two or more cells independently selected from hematopoietic stem cells and mesenchymal stem cells.

DETAILED DESCRIPTION OF THE INVENTION

Figure 1:
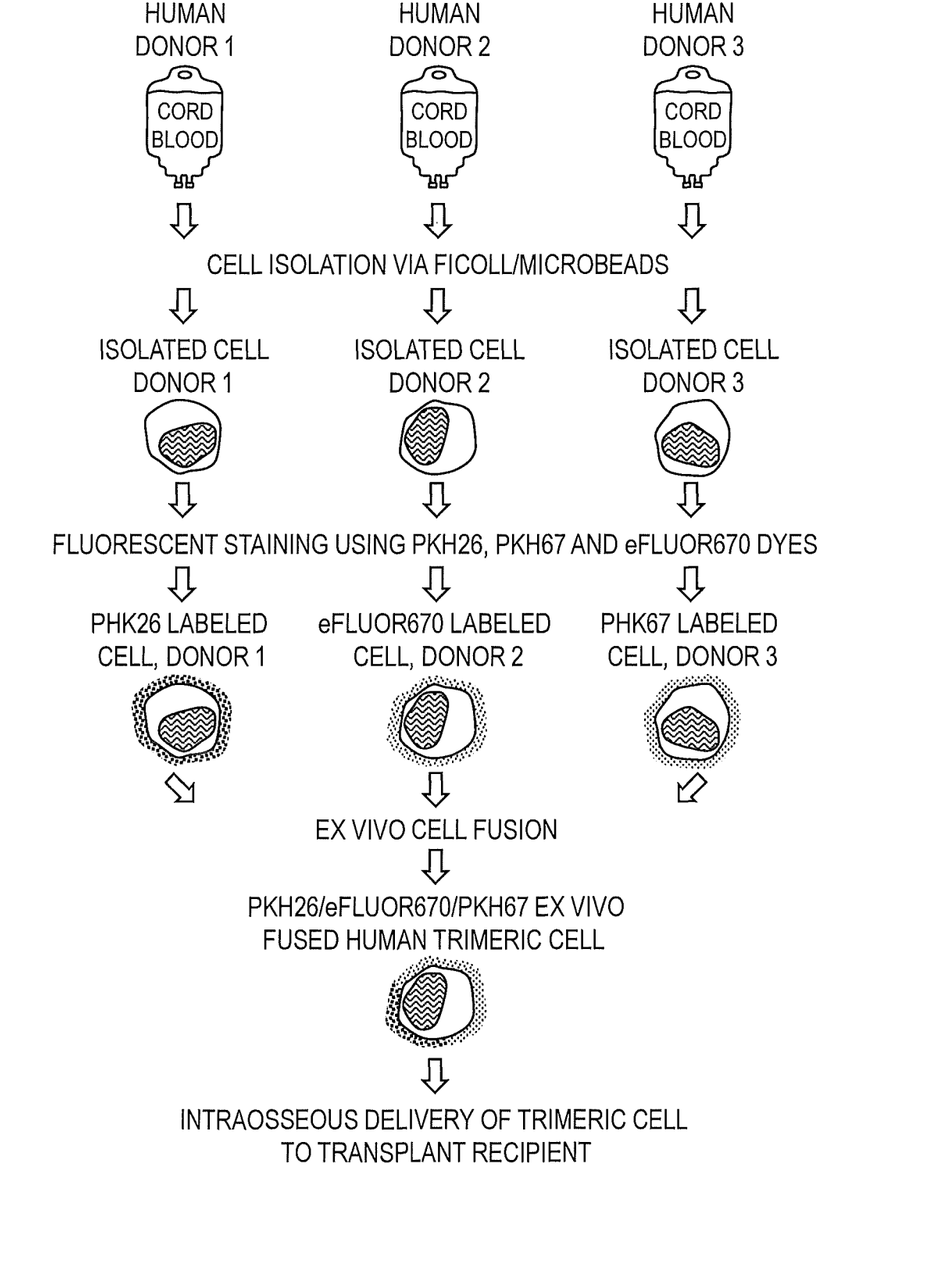
FIG. 1 shows the ex vivo fusion procedure to create Human Multi-Chimeric Cells (MCC). Human hematopoietic stem cells (HSC) are obtained from at least three or more related and/or unrelated donors. Prior to fusion, cells are fluorescently labeled with PKH26 (red) or PKH67 (green), or eFluor670 (magenta) dyes, respectively. Cell fusion of fluorescently labeled cells is performed using polyethylene glycol (PEG). Triple (PKH26 and PKH67 and eFluor670) stained cells that undergo fusion are selected via fluorescently-activated cell sorting (FACS). The multi-chimeric (trimera) cells are delivered through systemic-intraosseous injection into the transplant or immunodeficient patient.

Multi-chimeric cells for transplant therapy and for treating patients with immune deficiencies and genetic disorders have now been developed. Multi-chimeric cells of this invention were created by fusion of human hematopoietic stem cells (autologous and/or allogeneic), derived from at least three (trimera) or more (quadruple-chimera and multigeneration chimera etc.) related and/or unrelated donors (FIG. 1). Specifically, multiple-generations of chimeric cells were created via PEG-mediated ex-vivo fusion of cells of hematopoietic origin: hematopoietic stem cells (HSCs) or umbilical cord blood (UCB) cells or Bone Marrow (BM) cells or a combination of HSC and/or UCB and/or BM. The resulting multi-chimeric cells expressed on their surface the HLA antigens specific for the respective multiple cell donors. The microenvironment established by the multi-chimeric cells mitigate the side effects of immunosuppression and conditioning regimens and enhance HSC engraftment without GvHD. The instant approach will allow for treatment of a variety of immunological and genetic disorders.

Accordingly, this invention is a multi-chimeric cell, which is the product of an ex vivo fusion of three or more hematopoietic stem cells, mesenchymal stem cells, myoblasts, pericytes, or satellite cells, or a combination thereof, from three or more different donors, wherein said fusion is carried out in the presence of an exogenous fusogenic agent. For the purposes of this invention, a "multi-chimeric cell" is a cell that is constructed from cell fusion or hybridization (whole cell hybridization) of three or more biological cells (parent cells). While the multi-chimeric cell of this invention is referred to as "a multi-chimeric cell," said chimeric cell is intended to mean a single cell or a population of cells.

"Hematopoietic stem cells" or "HSCs" refer to clonogenic, self-renewing pluripotent cells capable of ultimately differentiating into all cell types of the hematopoietic system, including B cells T cells, NK cells, lymphoid dendritic cells, myeloid dendritic cells, granulocytes, macrophages, megakaryocytes, and erythroid cells. The marker phenotypes useful for identifying HSCs are commonly known in the art. For human HSCs, the cell marker phenotypes preferably include $CD34^+$ $CD38$ $CD90(Thy1)^+Lin^-$. For mouse HSCs, an exemplary cell marker phenotype is $Sca-1^+$ $CD90^+$ (see, e.g., Spangrude, et al. (1988) Science 1:661-673) or $c-kit^+$ $Thy^{lo}$ $Lin^-$ $Sca-1^+$ (see, Uchida, et al. (1998) J. Clin. Invest. 101(5):961-966). Alternative HSC markers such as aldehyde dehydrogenase (see Storms, et al. (1999) Proc. Nat'l Acad. Sci. 96:9118-23, AC133 (see Yin, et al. (1997) Blood 90:5002-12), and CD150 (SLAM) (see Kiel (2005) Cell 121(7):1109-21) may also find advantageous use. In certain embodiments, the hematopoietic stem cells are isolated from bone marrow, umbilical cord blood and/or peripheral blood.

"Mesenchymal stem cells" or "MSCs" are cells that can give rise to connective tissue, bone, cartilage, and cells in the circulatory and lymphatic systems. Mesenchymal stem cells are found in the mesenchyme, the part of the embryonic mesoderm that consists of loosely packed, fusiform or stellate unspecialized cells. Mesenchymal stem cells can be obtained by conventional methods and can be identified one or more of the following markers: CD29, $CD31^-$, $CD34^-$, $CD44$ $CD45^-$, CD51, CD73, CD90/Thy-1, CD105, CD166, Integrin al, PDGF Roc, Nestin, $Sca-1^+$, SCF R/c-Kit, STRO-1, and VCAM-1. In some embodiments, the mesenchymal stem cells are derived or obtained from bone marrow (BM) or adipose tissue (ASC). In particular embodiments, the mesenchymal stem cells are derived or obtained from human bone marrow.

As is conventional in the art, a "myoblast" refers to a primitive muscle cell having the potential to develop into a muscle fiber. Myoblasts are characterized by expression of desmin and CD56, and can be obtained from fetal or adult tissue using a method known in the art. See, e.g., WO 93/03768, which discloses the isolation of myoblasts from a crude cell population by flow cytometry (e.g., FACs). Alternatively, a myoblast can be obtained by growing and propagating muscle biopsy-derived myoblasts in culture. See, e.g., Springer, et al. (1997) In: Current Human Genetics. Unit 13.4, Boyle Ed. John Wiley & Sons, NY.

"Pericytes," as used herein, are multipotent cells associated with the walls of small blood vessels. Previous studies have shown that pericytes can differentiate into various cell types such as adipocytes, chondrocytes, fibroblasts and macrophages. Pericytes are characterized by the expression of one of the following markers: vimentin, neuro-glial 2 (NG2), platelet-derived growth factor receptor beta (PDGFR-β), and α-smooth muscle actin (α-SMA).

"Satellite cells" are mononucleated myoblasts of mature muscle fiber, and are responsible for postnatal muscle growth and regeneration in vivo. Markers of use in characterizing satellite cells include, but are not limited to, M-cadherin, CD34, and c-met. Satellite cells may be isolated from muscle tissue by known methods (see, e.g., US 2007/0224168).

As used herein, a donor is a subject who provides a cell used in the preparation of a multi-chimeric cell of this invention. The donor is preferably a healthy donor, i.e., an individual not suffering from a genetic disorder or disease. Further, the donor may be any mammal including a human, mouse, rat, dog, cat, horse, and the like. In particular embodiments, the donor is human.

The donor can be the genetic relative (e.g., parent or sibling) of a subject or a cell bank donor. Accordingly, in some embodiments, one or more the cells used in the generation of the multi-chimeric cell are autologous. In other embodiments, all of the cells used in the generation of the multi-chimeric cell are autologous. In further embodiments, one or more the cells used in the generation of the multi-chimeric cell are allogeneic. In yet other embodiments, all of the cells used in the generation of the multi-chimeric cell are allogeneic.

As used herein, "autologous" as it relates to isolation and transplantation of cells refers to cells in which the donor and recipient is the same individual. Thus, autologous cells are harvested from a subject and then returned to the same subject. In contrast, "allogeneic" cells are cells in which the donor and recipient are genetically non-identical individuals from the same species. By comparison, "xenogeneic" cells are cells in which the donor and recipient are of different species.

As indicated, the multi-chimeric stem cell of the invention is a fusion of three or more hematopoietic stem cells, mesenchymal stem cells, myoblasts, pericytes, or satellite cells, or a combination thereof. In some embodiments, the multi-chimeric stem cell is a fusion comprising or consisting of three cells selected from the group of hematopoietic stem cells, mesenchymal stem cells, myoblasts, pericytes, and satellite cells. In other embodiments, the multi-chimeric stem cell is a fusion comprising or consisting of four, five, six, seven, eight, nine or 10 cells selected from the group of hematopoietic stem cells, mesenchymal stem cells, myoblasts, pericytes, and satellite cells. In embodiments directed to the fusion of three cells, particular combinations of cells are provided in Table 1.

TABLE 1

| Cell 1 | Cell 2 | Cell 3 |
|---|---|---|
| HSC | HSC | HSC |
| HSC | HSC | MSC |

TABLE 1-continued

| Cell 1 | Cell 2 | Cell 3 |
|---|---|---|
| HSC | MSC | MSC |
| HSC | HSC | Pericyte |
| HSC | MSC | Pericyte |
| HSC | Pericyte | Pericyte |
| Myoblast | Myoblast | Myoblast |
| Myoblast | Myoblast | MSC |
| Myoblast | MSC | MSC |
| Myoblast | MSC | Satellite cell |
| Myoblast | Myoblast | Satellite cell |
| Myoblast | Satellite cell | Satellite cell |

In embodiments directed to the fusion of four cells, combinations of four cells are provided in Table 2.

TABLE 2

| Cell 1 | Cell 2 | Cell 3 | Cell 4 |
|---|---|---|---|
| HSC | HSC | HSC | HSC |
| HSC | HSC | MSC | MSC |
| HSC | MSC | MSC | Pericyte |
| HSC | HSC | Pericyte | Pericyte |
| HSC | MSC | Pericyte | Pericyte |
| HSC | Pericyte | Pericyte | Pericyte |
| Myoblast | Myoblast | Myoblast | Myoblast |
| Myoblast | Myoblast | MSC | MSC |
| Myoblast | MSC | MSC | MSC |
| Myoblast | MSC | Satellite cell | Satellite cell |
| Myoblast | Myoblast | Satellite cell | Satellite cell |
| Myoblast | Satellite cell | Satellite cell | Satellite cell |

In some embodiments, the multi-chimeric stem cell is an ex vivo fusion of a hematopoietic stem cell and two cells independently selected from hematopoietic stem cells, mesenchymal stem cells and pericytes. In a particular embodiment, the multi-chimeric stem cell is an ex vivo fusion of a hematopoietic stem cell and two cells independently selected from hematopoietic stem cells and mesenchymal stem cells. In another embodiment, the multi-chimeric stem cell is an ex vivo fusion of a hematopoietic stem cell, a mesenchymal stem cell and a pericyte. In another particular embodiment, the multi-chimeric stem cell is an ex vivo fusion of three hematopoietic stem cells.

In other embodiments, the multi-chimeric stem cell is an ex vivo fusion of a myoblast and two cells independently selected from mesenchymal stem cells, myoblasts and satellite cells, or a combination thereof. In a particular embodiment, the multi-chimeric stem cell is an ex vivo fusion of a myoblast, a mesenchymal stem and a satellite cell. In another particular embodiment, the multi-chimeric stem cell is an ex vivo fusion of three myoblasts.

The cells used in the preparation of the multi-chimeric stem cell of this invention can be isolated and optionally purified. As used herein the term "isolated" is meant to describe a cell of interest that is in an environment different from that in which the element naturally occurs. "Purified" as used herein refers to a cell removed from an environment in which it was produced and is at least 60% free, preferably 75% free, and most preferably 90% free from other components with which it is naturally associated or with which it was otherwise associated with during production.

Purification and/or identification of cells of interest can be achieved through any means known in the art, for example immunologically. Histochemical staining, flow cytometry, fluorescence activated cell sorting (FACS), western blot analysis, enzyme-linked immunosorbent assay (ELISA), density gradient separation (e.g., FICOLL®, polysucrose 400), immunomagnetic bead separation, or combinations thereof may be used. Flow immunocytochemistry may be used to detect cell-surface markers, immunohistochemistry (for example, of fixed cells) may be used for intracellular or cell-surface markers. Western blot analysis may be conducted on cellular extracts. Enzyme-linked immunosorbent assay may be used for cellular extracts or products secreted into the medium. Antibodies for the identification of stem cell markers may be obtained from commercial sources, for example from Chemicon International, (Temecula, Calif.).

The multi-chimeric stem cell of this invention is prepared by ex vivo contacting three or more cells from three or more different donors with an exogenous fusigenic agent thereby promoting ex vivo fusion of the three or more different donor cells. By "ex vivo" it is meant that cells are manipulated outside of the body. Cell fusion is a process in which three or more cells merge into one by fusing their plasma membranes. Multi-chimeric stem cells can be prepared using fusogenic agents and methods known in the art, including, but not limited to, exposure of cells to fusion-promoting chemicals, such as polyethylene glycol (PEG); the use of inactivated virus, such as Sendai virus; and the use of electrical stimulation. See, e.g., Kennett (1979) *Methods Enzymol.* 58:345-359 for a review of the commonly used methods based upon Sendai virus induced cell fusion, or cell fusion induced by polyethylene glycol (PEG). Briefly, cells to be fused are incubated with a fusogenic agent, such as Sendai virus or PEG. Centrifugation or agitation may be used to encourage clumping and close apposition of the cell membranes. Variables such as time, temperature, cell concentration and fusogenic agent concentration may be optimized for each cell combination. With respect to electro fusion, short electric pulses are passed through mixtures of cells to stimulate fusion. See, e.g., Neil & Zimmermann (1993) *Methods Enzymol.* 220:174-196. In certain embodiments, the multi-chimeric stem cell is prepared by polyethylene glycol cell fusion.

Prior to fusion, the donor cells may or may not be cultured to increase their number. Further, the donor cells may or may not be labeled (e.g., with a membrane dye) to monitor fusion of the donor cells. By way of illustration, HSCs from a first donor are labeled with PKH26 (emission at 567 nm), MSCs from a second donor are labeled with eFluor670 (emission at 670 nm), and pericytes from a third donor are labeled with PKH67 (emission at 502 nm) such that upon fusion, the fused cell fluoresces at 502, 567 and 670 nm (FIG. 1). To identify the multi-chimeric cell of this invention, the fusion cell is selected via cell sorting, e.g., fluorescently-activated cell sorting (FACS). Once identified, the multi-chimeric cells can be cryopreserved, stored and banked as a cell line. Alternatively, successful fusion of the three or more cells can be assessed by morphologicial, phenotypical or genotypical characterization.

The multi-chimeric stem cell of this invention is of particular use in the treating immune deficiencies and genetic disorders. Accordingly, this invention also provides a method for treating an immune deficiency or genetic disorder in a subject in need thereof by administering to the subject the multi-chimeric stem cell of the invention or a composition containing the multi-chimeric stem cell in an amount effective to treat the immune deficiency or genetic disorder. "Treating" a subject having a disease or disorder means accomplishing one or more of the following: (a) reducing the severity of the disease; (b) arresting the development of the disease or disorder; (e) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (g) improving survival. In some embodiments, the multi-chimeric stem cell used in the method of this invention is a fusion of three or more hematopoietic stem cells, mesenchymal stem cells or myoblasts from three or more different donors.

Immune deficiencies and genetic disorders, which may be treated in accordance with this invention include bone marrow failures, Adenosine Deaminase (ADA) deficiency, Severe Combined Immunodeficiency (SCID), DiGeorge Syndrome, Ataxia Telangectasia, muscular dystrophies, type diabetes, Gaucher disease, leukemia, aplastic anemia, lymphoma and multiple myeloma. In certain embodiments, the immune deficiencies and genetic disorders are selected from bone marrow failures, muscular dystrophies, sickle cell anemia, leukemia and type I diabetes. In other embodiments, the genetic disorder is muscular dystrophy.

Muscular dystrophies are a group of genetic diseases characterized by progressive weakness and degeneration of the skeletal muscles that control movement. Examples of muscular dystrophies include Duchenne Muscular Dystrophy, Becker Muscular Dystrophy, Limb Girdle Muscular Dystrophy, Myotonic Muscular Dystrophy, Facioscapulohumeral Muscular Dystrophy, Oculopharyngeal muscular dystrophy, Emery-Dreifuss muscular dystrophy, Fukuyama-type congenital muscular dystrophy, Miyoshi myopathy, Ullrich congenital muscular dystrophy, Steinert Muscular Dystrophy. In certain embodiments, the muscular dystrophy is Duchenne muscular dystrophy (DMD). In particular embodiments, the muscular dystrophy is treated with a multi-chimeric cell that is a fusion of a myoblast and two or more cells independently selected from mesenchymal stem cells, myoblasts and satellite cells.

In another embodiment, the immune deficiency or genetic disorder is sickle cell anemia. In accordance with this embodiment, the sickle cell anemia is treated with a multi-chimeric cell that is a fusion of a hematopoietic stem cell and two or more cells independently selected from a hematopoietic stem cell and mesenchymal stem cell.

In so far as the multi-chimeric cells of the invention provide tolerogenic and immunomodulatory effects in the context of organ and HSC transplantation, this invention also includes a method of preventing the development of GvHD or reducing the severity of GvHD in a subject receiving an allogeneic hematopoietic stem cell transplant or organ transplant. As is known in the art, "Graft-versus-host response" or "GVH" or "GVHD" refers to a cellular response that occurs when lymphocytes of a different MHC class are introduced into a host, resulting in the reaction of the lymphocytes against the host. In accordance with this method, a subject receiving an allogeneic hematopoietic stem cell transplant or organ transplant is administered an effective amount of a multi-chimeric cell to prevent the development of or reduce the severity of GvHD.

The multi-chimeric cell may be separately administered to the subject and/or included as a part of the hematopoietic stem cell transplant or organ transplant. Treatment with the multi-chimeric cell of the invention can significantly reduce the incidence of GvHD and its severity and prevent allograft rejection, ameliorate immune responses and/or reduce/eliminate the need for life-long immunosuppression in the transplant patients. In this respect, the multi-chimeric cell of the invention is of use in preventing the development of GvHD associated symptoms and signs of the various organs and systems, including the skin, nails, mouth, eyes, female genitalia, gastrointestinal tract, liver, lungs, muscles, fascia, joints and the like. In a particular embodiment, the GvHD is treated with a multi-chimeric cell that is a fusion of a hematopoietic stem cell and two or more cells independently selected from hematopoietic stem cells and mesenchymal stem cells.

In accordance with the methods of treatment herein, a multi-chimeric cell or composition containing the same is administered to a subject in need of treatment. In some embodiments, a combination of multi-chimeric cell of this invention can be administered. The multi-chimeric cell or combination of cells can be administered by engraftment, wherein the cells are injected into the subject, for example, intravenously, intramuscularly, intraarterially, intraosseously and the like. In particular embodiments, the multi-chimeric stem cell is administered by intraosseous, intravenous, or intramuscular injection. In certain embodiments, administration involves engrafting about $10^2$, $10^4$, $10^6$, $10^7$, $10^8$, $10^9$, $10^{10}$, $10^{12}$, or more cells. The number of cells engrafted may be chosen based on the route of administration and/or the severity of the condition for which the cells are being engrafted. Advantageously, the multi-chimeric stem cell of this invention will successfully engraft and complement genetic/immunogenic defects, and provide tolerogenic and immunomodulatory effects in the context of organ and HSC transplantation.

Compositions containing the multi-chimeric cell or combinations of multi-chimeric cell can be prepared by combining the cell or combination of cells with a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and the like. The use of such media and agents for pharmaceutically active substances is well known in the art. Except insofar as any conventional media or agent is incompatible with the cells of the present disclosure, its use in therapeutic compositions is contemplated. Pharmaceutical compositions can be determined by one skilled in the art depending upon, for example, the intended route of administration, delivery format and desired dosage. See, for example, Remington, The Science and Practice of Pharmacy, $22^{nd}$ Edition, 2012.

The compositions of the invention can be incorporated in an injectable formulation. The formulation may also include the necessary physiologically acceptable carrier material, excipient, lubricant, buffer, surfactant, antibacterial, bulking agent (such as mannitol), antioxidants (ascorbic acid or sodium bisulfite) and the like.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials may include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA; complexing agents (such as caffeine, polyvinylpyrrolidone, beta-cyclodextrin or hydroxypropylbeta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PEG, sorbitan esters, polysorbates such as polysorbate 20 and polysorbate 80, TRITON (surfactant), trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, Remington, The Science and Practice of Pharmacy, Id.

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefore. Pharmaceutical compositions of the invention may be prepared for storage by mixing the selected composition having the desired degree of purity with optional formulation agents (Remington, The Science and Practice of Pharmacy, Id.) in the form of a lyophilized cake or an aqueous solution.

The cell or composition can be provided by sustained release systems, by encapsulation or by implantation devices. The compositions may be administered by bolus injection or continuously by infusion, or by implantation device. The composition also can be administered locally via implantation of a membrane, sponge or another appropriate material onto which the cell or cells have been absorbed or encapsulated. Where an implantation device is used, the device may be implanted into any suitable tissue or organ. The injections may be given as a one-time treatment, repeated (daily, weekly, monthly, annually etc.) in order to achieve the desired therapeutic effect.

Cell encapsulation methodology has been previously described which allows transplantation of encapsulated cells in treatment of Parkinson's disease (Tresco, et al. (1992) *ASAIO J.* 38:17-23) or Amyotrophic lateral sclerosis (Aebischer, et al. (1996) *Hum. Gene Ther.* 7:851-860). In accordance with this embodiment, cells are encapsulated by compounds which form a microporous membrane. Capsules, for example approximately 1 cm in length, containing the cells of interest may be prepared employing a hollow microporous membrane fabricated from poly-ether-sulfone (PES) (Akzo Nobel Faser A G, Wuppertal, Germany; Déglon, et al. (1996) *Hum. Gene Ther.* 7:2135-2146).

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like.

Supplementary active ingredients also can be incorporated into the compositions. The active compositions of the present disclosure may include classic pharmaceutical preparations. Administration of these compositions according to the present disclosure will be via any common route so long as the target tissue is available via that route.

As used herein, the term "amount effective," "effective amount" or a "therapeutically effective amount" refers to an amount of the cell or composition of the invention sufficient to achieve the desired result. The amount of the cell or composition which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect.

The present invention is also directed to a kit for the treatment of an immune deficiency or genetic disorder and/or preventing or ameliorating GvHD. The kit is useful for practicing the inventive methods described herein. The kit is an assemblage of materials or components, including at least one of the inventive compositions. Thus, in some embodiments the kit includes a fusogenic agent for carrying out ex vivo cell fusions, and three or more donor cells (e.g., donor cells from a cell bank) selected from the group of hematopoietic stem cells, mesenchymal stem cells, myoblasts, pericytes, satellite cells from different donors, and optionally materials for obtaining donor cells, as described above.

The exact nature of the components configured in the inventive kit depends on its intended purpose. For example, some embodiments are configured for the purpose of treating a muscular dystrophy. In one embodiment, the kit is configured particularly for the purpose of treating human subjects. In another embodiment, the kit is configured particularly for the purpose of treating adult, human subjects. In another embodiment, the kit is configured particularly for the purpose of treating children. In another embodiment, the kit is configured particularly for the purpose of treating DMD and can include a myoblast and two or more cells independently selected from mesenchymal stem cells, myoblasts, and satellite cells. In another embodiment, the kit is configured particularly for the purpose of treating GvHD and can include a hematopoietic stem cell and two or more cells independently selected from hematopoietic stem cells and mesenchymal stem cells. In another embodiment, the kit is configured particularly for the purpose of treating sickle cell anemia and can include a hematopoietic stem cell and two or more cells independently selected from hematopoietic stem cells and mesenchymal stem cells. In another embodiment, the kit is configured particularly for the purpose of providing continuous daily use dosages. In another embodiment, the kit is configured particularly for the purpose of providing as needed use dosages. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome, such as to treat muscular dystrophy, to treat sickle cell anemia, or to treat GvHD. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit. The packaging material is constructed by well-known methods, preferably to provide a sterile, contaminant-free environment. The packaging materials employed in the kit are those customarily utilized in therapeutic treatment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

The following non-limiting examples are provided to further illustrate the present invention.

Example 1: Ex Vivo Generation of Human Multi-Chimeric Cells

Multi-Chimeric Cells (MCC) are generated by ex vivo cell fusion of human hematopoietic cells from three or more related and/or unrelated donors and from one or more sources of hematopoietic stem cells, i.e., bone marrow ("BM"), peripheral blood ("PB"), and/or umbilical cord blood ("UCB"), e.g., from a commercially available source.

Mononuclear cells were isolated and purified from three unrelated donors. Subsequently, the mononuclear cells from the three donors were each pre-stained with a different fluorescent cell membrane dye (i.e., PKH 26 and PKH 67 and CELLVUE® Claret (far red fluorescent dye); Sigma Aldrich). Fluorescently labeled cells were mixed in a ratio of 1:1:1 and fused using polyethylene glycol. Based on the triple staining, the MCC were sorted (purity 80-90%).

To confirm fusion, triple labeled (PKH26, PKH67 and CELLVUE® Claret) chimeric cells are evaluated using confocal microscopy and flow cytometry. The viability, genotype and phenotype stability of multi-chimeric cells were evaluated using standard assays. In particular, short tandem repeat PCR was used for genotype characterization. The results of these analyses are presented in Table 3.

TABLE 3

| Sample | D5S818 | D7S820 | TH01 | AMEL | TPOX | CSF1PO | vWA | D21S11 |
| --- | --- | --- | --- | --- | --- | --- | --- | --- |
| Male | 12, 13 | 8, 10 | 9 | Y | 6, 12 | 10, 12 | 16, 17 | 27 |
| Female | 12, 13 | 11 | 6, 7 | X | 9 | 10, 11 | 15, 18 | 27, 30 |
| Female | 12 | 10, 11 | 9 | X | 9 | 12 | 16, 18 | 29, 32.2 |
| Fusion | 12, 13 | 8, 10, 11 | 6, 7, 9 | X, Y | 6, 8, 12 | 10, 11, 12 | 15, 16, 17, 18 | 27, 29, 30, 32.2 |

Currently there is no available therapy to support organ and HSC transplant without the side effects of immunosuppression and development of GvHD. Multi-chimeric cell therapy will have a tremendous impact on the elimination of side effects of immunomodulatory protocols required to prevent organ and HSC transplant rejection. This therapy will significantly increase the life-span and quality of life of transplant patients. The risk of GvHD, the most limiting and dangerous complication of HSC transplantation, will be significantly decreased in patients treated with multi-chimeric cells. Therapy with immuno-privileged chimeric cells will provide more effective HSC engraftment and reconstitution of the bone marrow (BM) compartment, thus leading to tolerance induction and better outcomes of transplant recipients and patients with immune deficiencies.

Unique characteristics of MCCs include their ability to express hematopoietic and/or other markers (e.g., myoblast) of the parent cells as well as tolerogenic cytokines. Additionally, chimeric cells can be cryopreserved, stored and banked, making them immediately available for the acute, as well as boosting and long-term therapy. Due to these unique properties, the MCC therapy has important advantages over other stem cell-based strategies.

Example 2: Fusion and Phenotypic Characterization of Human Umbilical Cord Blood Cells Thirty individual fusions of human UCB cells from three unrelated donors were performed as shown in FIG. 1. Confocal microscopy and flow cytometry confirmed that ex vivo fusion occurred by the presence of triple (PKH26/PKH67/eFluor 670) fluorescently labeled MCCs. Additional phenotypic characteristics of the MCCs were also evaluated. In particular, it was found that the ex vivo fusion procedure did not change the expression of CD4, CD90, CD45 and CD19 by the MCCs when compared to controls, i.e., eFluor670 proliferation dye-labeled UCB cells. Furthermore, 90-95% of the MCCs were viable, as determined by Trypan Blue staining, and proliferative properties were demonstrated by in vivo colony forming unit assays including multicentric, multipotential granulocyte, erythroid, macrophage, megakaryocyte colony forming units (CFU-GEMM), granulocyte colony forming unit (CFU-G), granulocyte-macrophage colony forming unit (CFU-GM), macrophage colony forming unit (CFU-M), and erythroid burst-forming unit (BFU-E) assays. Genotype analysis of the MCCs, using serological HLA typing, confirmed the presence of alleles specific for each of the three unrelated donors in the genetic material of MCC (Table 4).

TABLE 4

| | Allele | | | | | | |
|---|---|---|---|---|---|---|---|
| Donor | A | B | C | Bw | DRB1* | DQB1* | DR51, DR52, DR53 |
| 1 | 30, 74 | 14 (65), 15 (71) | 03 (10), 08 | 6 | 03 (17) | 02 | 52 |
| 2 | 02, 66 | 07, 45 | 07, 16 | 6 | 03 (17), 13 | 02, 06 | 52 |
| 3 | 03, 11 | 07, 15 (75) | 07, 08 | 6 | 15 | 06 | 51 |
| Fusion | 30, 74, 03, 11, 02, 66 | 14 (65), 15 (71), 07, 45, 15 (75) | 03 (10), 08, 07, 16 | 6 | 15, 13, 03 (17) | 02, 06 | 51, 52 |

Genotype analysis of the MCCs using STR PCR further confirmed the presence of markers specific for each of the three unrelated donors in the genetic material of the MCCs (Table 5).

TABLE 5

| | Marker | | | | | | | |
|---|---|---|---|---|---|---|---|---|
| Donor | TH01 | D21S11 | D5S818 | D13S317 | D7S820 | D16S539 | vWA | TPOX |
| 1 | 7 | 28, 32 | 11, 12 | 11, 12 | 10 | 9, 13 | 18, 21 | 8 |
| 2 | 6 | 29, 31.2 | 11, 14 | 8, 12 | 8, 11 | 11 | 16, 17 | 8, 9 |
| 3 | 6, 7 | 30, 35 | 9, 12 | 11, 12 | 7, 9 | 10, 12 | 15, 18 | 6, 11 |
| Fusion | 6, 7 | 28, 29, 30, 31.2, 32, 35 | 9, 11, 12, 14 | 8, 11, 12 | 7, 8, 9, 10, 11 | 9, 10, 11, 12, 13 | 15, 16, 17, 18, 21 | 6, 8, 9, 11 |

Tumorigenicity of the MCCs in an NSG mouse model was also evaluated. Mice were administered MCC via intraosseous (IO) or intravenous (IV) routes as outlined in Table 6.

TABLE 6

| Groups | Route of Cell Delivery | Number of Animals Injected | Number of Animals to Complete the Group |
|---|---|---|---|
| Control Animals Receiving Mononuclear UCB Cells Derived from 3 Unrelated Donors | | | |
| 1 | IO | 5 | 1 |
| 2 | IV | 3 | 3 |
| MCC | | | |
| 4 | IO | 5 | 1 |
| 5 | IV | 0 | 6 |

Clinical observations of NSG mice at day 90 post-injection indicated that the animals were active, with normal weight gain, normal fur and without tumor-like growths, including at the injection site as determined by. palpation. Further, magnetic resonance imaging (MRI) of NSG mice 90 days following cell delivery indicated no tumor-like structures in mice receiving a mixture of unfused human cord blood cells derived from 3 unrelated donors or mice receiving fused MCC.

What is claimed is:

1. A multi-chimeric cell comprising an ex vivo fusion of three or more cells selected from the group consisting of hematopoietic stem cells, mesenchymal stem cells, myoblasts, pericytes, satellite cells, and combinations thereof, from three or more different donors, wherein the multi-chimeric cell is in a pharmaceutically acceptable carrier or aqueous medium; and each of the three or more cells are labeled with a different label and the multi-chimeric cell resulting from the fusion can be isolated by cell sorting based on the presence of each of the different labels; and at least one of the three or more cells is a mesenchymal stem cell, myoblast, pericyte, or satellite cell.

2. The multi-chimeric cell of claim 1, consisting of an ex vivo fusion of at least one hematopoietic stem cell and two or more mesenchymal stem cells.

3. The multi-chimeric cell of claim 1, wherein the hematopoietic stem cells are isolated from bone marrow, umbilical cord blood, peripheral blood, or a combination thereof.

4. The multi-chimeric cell of claim 1, wherein the donors are related, unrelated, or a combination thereof.

5. The multi-chimeric cell of claim 1, consisting of an ex vivo fusion of at least one hematopoietic stem cell and two or more cells independently selected from mesenchymal stem cells and pericytes.

6. The multi-chimeric cell of claim 5, consisting of an ex vivo fusion of a hematopoietic stem cell, a mesenchymal stem cell and a pericyte.

* * * * *